(12) United States Patent
Alul

(10) Patent No.: US 9,616,211 B2
(45) Date of Patent: Apr. 11, 2017

(54) ROLLER DEVICE

(71) Applicant: NEW PERMANENT MAKEUP LTD., Haifa (IL)

(72) Inventor: Moshe Alul, Kiryat Ata (IL)

(73) Assignee: NEW PERMANENT MAKEUP LTD., Haifa (IL)

(*) Notice: Subject to any disclaimer, the term of this patent is extended or adjusted under 35 U.S.C. 154(b) by 260 days.

(21) Appl. No.: 14/359,708

(22) PCT Filed: Nov. 21, 2012

(86) PCT No.: PCT/IL2012/000376
§ 371 (c)(1),
(2) Date: May 21, 2014

(87) PCT Pub. No.: WO2013/076715
PCT Pub. Date: May 30, 2013

(65) Prior Publication Data
US 2014/0343591 A1 Nov. 20, 2014

Related U.S. Application Data

(60) Provisional application No. 61/561,949, filed on Nov. 21, 2011.

(51) Int. Cl.
A61B 17/34 (2006.01)
A61M 37/00 (2006.01)
(Continued)

(52) U.S. Cl.
CPC ........ *A61M 37/0015* (2013.01); *A61M 5/178* (2013.01); *A61M 5/46* (2013.01);
(Continued)

(58) Field of Classification Search
CPC ...... A61M 2037/0023; A61M 37/0015; A61M 5/46; A61M 37/0076
See application file for complete search history.

(56) References Cited

U.S. PATENT DOCUMENTS 5,713,890 A * 2/1998 Chasan ................. A61B 90/39
604/47
5,964,729 A * 10/1999 Choi .................... A61B 17/205
604/47
(Continued)

FOREIGN PATENT DOCUMENTS

EP 2 286 760 2/2011
KR 2009/0073716 7/2009
(Continued)

OTHER PUBLICATIONS

Sule, Ashwini Kulkarni, "Micro Hair Tattooing", Buzzle.com, published Apr. 8, 2011, 2 pages.
(Continued)

Primary Examiner — Gregory Anderson
(74) Attorney, Agent, or Firm — Nixon & Vanderhye P.C.

(57) ABSTRACT

The invention relates to a device for inserting pigment into the skin comprising a roller head unit comprising 2 or more distal arms; a rotatable structure comprising needles extending therefrom, attached to said roller head unit between said distal arms; a tubular member attached to the proximal end of said roller head unit; an elastic element placed within the distal portion of the inner lumen of said tubular member; a pin placed within said tubular member proximal to said elastic element.

20 Claims, 22 Drawing Sheets

(51) Int. Cl.
    *A61M 5/178*     (2006.01)
    *A61M 5/46*     (2006.01)
    *A61M 5/00*     (2006.01)

(52) U.S. Cl.
    CPC .......... *A61M 37/0076* (2013.01); *A61M 5/00* (2013.01); *A61M 2037/0023* (2013.01); *A61M 2210/04* (2013.01)

(56) References Cited

U.S. PATENT DOCUMENTS

| | | |
|---|---|---|
| 2007/0073217 A1 | 3/2007 | James |
| 2007/0157400 A1 | 7/2007 | Ali |
| 2009/0118698 A1 | 5/2009 | Liebl |
| 2010/0292723 A1 | 11/2010 | Lee |

FOREIGN PATENT DOCUMENTS

| | | |
|---|---|---|
| KR | 2009-0110769 | 10/2009 |
| KR | 2011-0103111 | 9/2011 |
| WO | WO 2008/004781 | 1/2008 |

OTHER PUBLICATIONS

International Search Report and Written Opinion for PCT/IL2012/000376, mailed Mar. 21, 2013.
Sule, A.K., "Micro Hair Tattooing", Retrieved from the Internet: http/www.buzzle, (Apr. 8, 2011).

\* cited by examiner

Section A-A

Section A-A

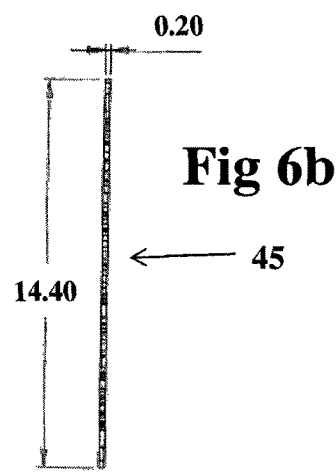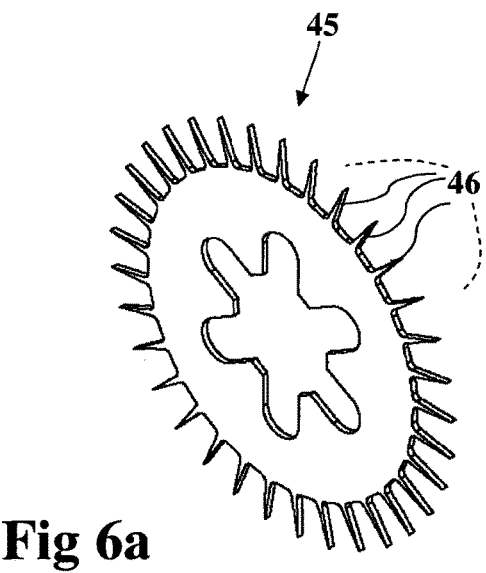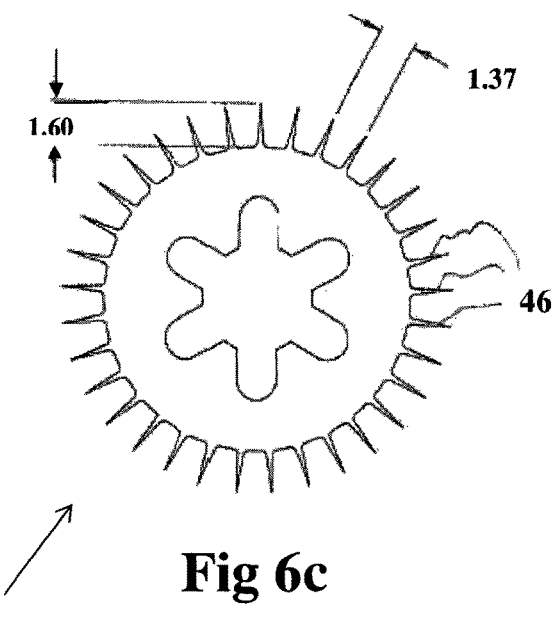
Fig 6b
Fig 6a
Fig 6c

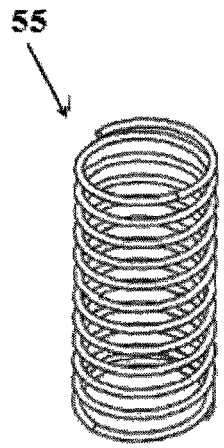
Fig 8a
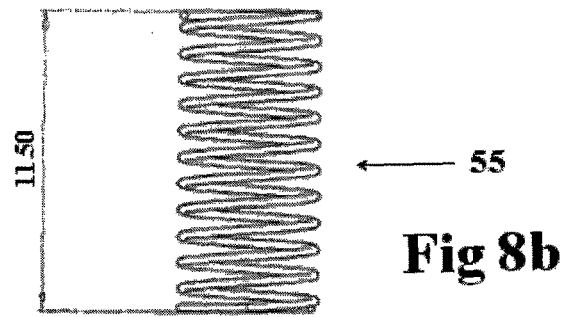
Fig 8b
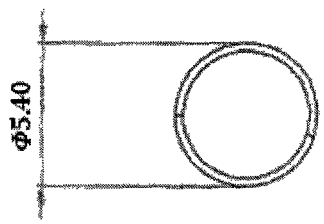
Fig 8c
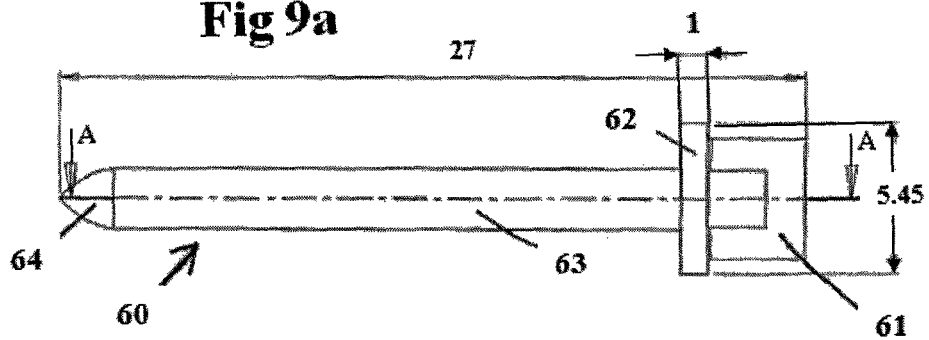

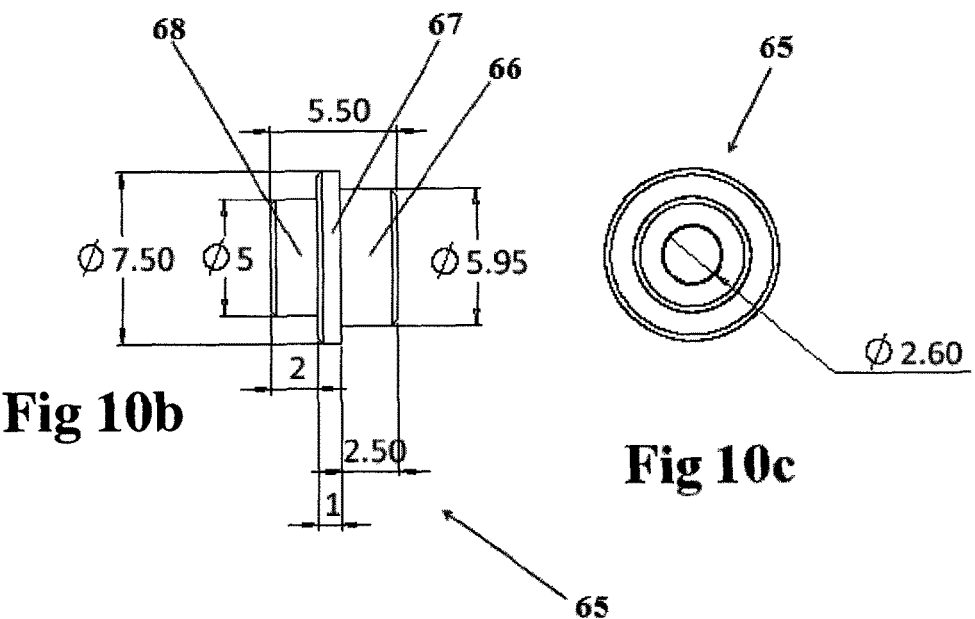
Fig 10b
Fig 10c
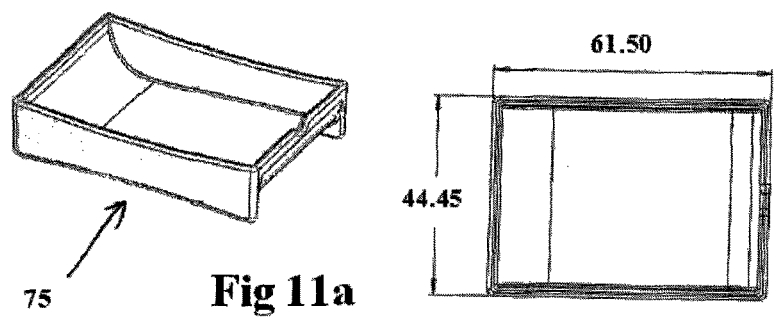
Fig 11a
Fig 11b
Fig 11c

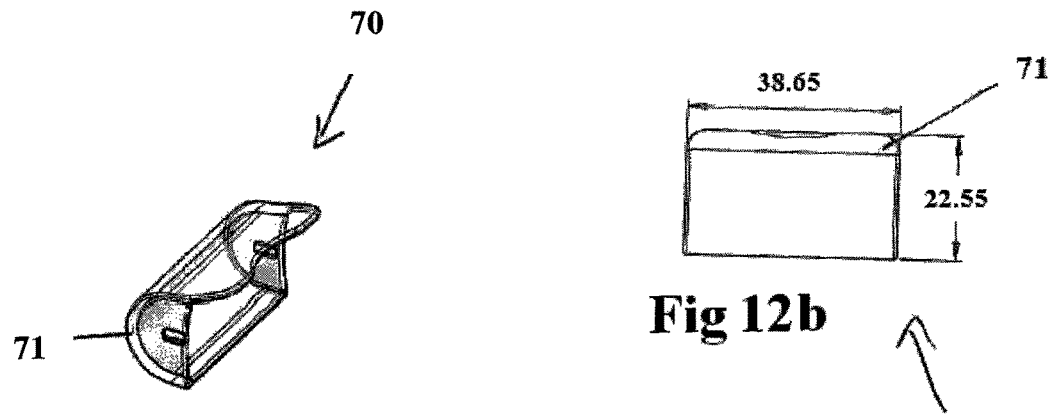
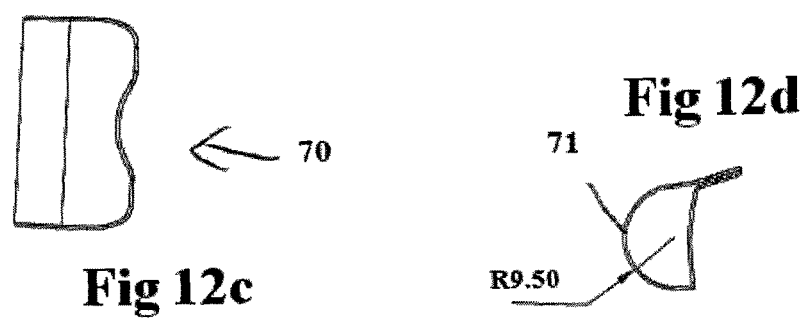
Fig 12a
Fig 12b
Fig 12c
Fig 12d

SECTION A-A

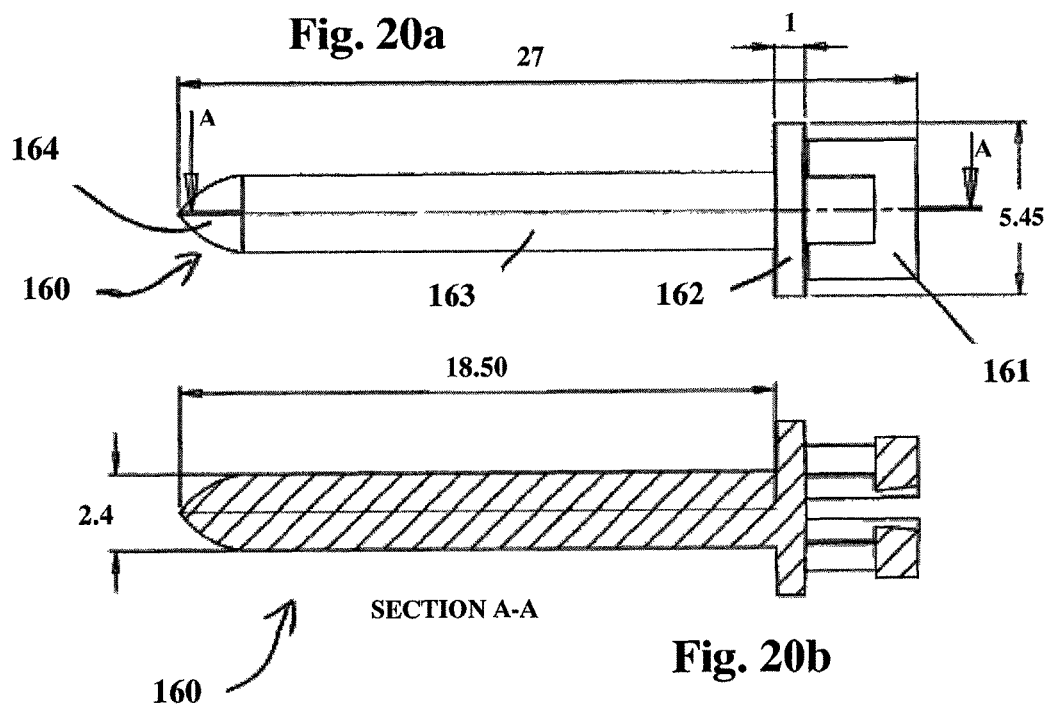
Fig. 20a
Fig. 20b
SECTION A-A
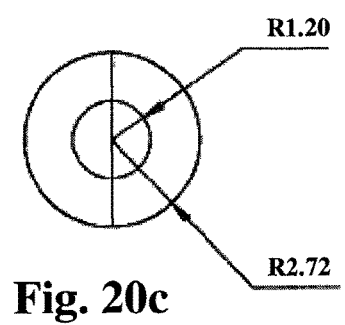
Fig. 20c

ROLLER DEVICE

This application is the U.S. national phase of International Application No. PCT/IL2012/000376, filed 21 Nov. 2012, which designated the U.S. and claims the benefit from U.S. Provisional Application No. 61/561,949, filed 21 Nov.2011, the entire contents of each of which are hereby incorporated by reference.

FIELD OF THE INVENTION

The present invention relates to the field of permanent makeup. More particularly, the present invention relates to a device and method for inserting pigment in the skin giving an appearance of hair follicles on the skin.

BACKGROUND OF THE INVENTION

Many people suffer from partial hair loss on the head scalp. Several areas in various shapes on the scalp do not enable the growth of hair on them, causing a lack of comfort in some people. Attempts have been made to hide or disguise these areas by coloring them or by sticking artificial hair on to them.

US 2007/0157400 relates to a method for cosmetically coloring scalp balding areas involving drawing hair into preferred hairdressing form to exposed balding areas, and bringing cosmetic core end of elongated pencils against the balding areas to color the exposed sections.

US 2010/0292723 relates to a disk needle roller for forming micro-holes in a surface of skin by using micro-needles to stimulate and assist regeneration of the skin.

US 2007/0073217 relates to an apparatus for delivering a bioactive material to a subterranean layer of a skin. Architecture is provided that includes a head including one or more needles that are operable to penetrate the stratum corneum of the skin.

US 2009/0118698 relates to a device and a process for introducing an active ingredient into the skin. The device comprises a roller that is mounted to rotate around the longitudinal axis thereof and on whose outside peripheral surface a number of needles project radially outward. After the active ingredient has been applied on the skin, the roller rolls over the skin. In this case, the needles penetrate the skin and open up fine channels there, through which the active ingredient penetrates through the epidermis up to the dermis.

None of the prior art devices and methods provides an efficient manner of giving a natural appearance of hairs or hair follicles within bald areas of the skin.

It is therefore an object of the present invention to provide a method and means for giving bald areas on the scalp a natural appearance of hairs and hair follicles.

Other objects and advantages of the present invention will become apparent as the description proceeds.

SUMMARY OF THE INVENTION

The present invention relates to a device for inserting pigment within the second layer of the skin, i.e. the dermis, giving an appearance of hair or hair follicles on the skin.

The present invention device comprises a rotating unit comprising needles or micro needles. The device is connected to a vibrating pigmentation treatment device. The unique structure of the device and connection to the vibrating pigmentation treatment device enables the roller unit to vibrate and thus when rolling the roller unit on the skin the roller needles, that were pre-dipped in pigment, penetrate and exit the skin thus inserting the pigment into the dermis causing colored "dots" in the skin giving the appearance of hairs and hair follicles. The vibration effect assists in pushing the needles into the hard scalp skin.

The device comprises said rotating unit connected by both ends to two arm elements that are attached to a unified portion connected to an elongated portion used as a handle fit for holding it and rolling the rotating unit on the skin. The elongated portion connects to the vibrating pigmentation treatment device.

The present invention relates to a device for inserting pigment into the skin comprising:
  a. a roller head unit comprising 2 or more distal arms;
  b. a rotatable structure comprising needles extending therefrom, attached to said roller head unit between said distal arms;
  c. a tubular member attached to the proximal end of said roller head unit;
  d. an elastic element placed within the distal portion of the inner lumen of said tubular member;
  e. a pin placed within said tubular member proximal to said elastic element;
Preferably, the rotatable structure comprises:
  a. one or more needle discs, each needle disc comprising a plurality of needles radially projected from the outer circumference of said needle discs, wherein said needle discs are mounted on the shaft of a female element;
  b. a male element placed in said female element.

Preferably, the roller device further comprises one or more spacer roller discs mounted on the shaft of the female element.

Preferably, the roller device further comprises depressions on the base of the male and female elements, and wherein the roller head unit distal arms comprise pins placed in said depressions.

Preferably, the elastic element is a spring.

Preferably, the pin extends out of the tubular member distally.

Preferably, each needle disc comprises 12-16 needles, and wherein the distance between the roller head unit distal arms is 12-18 mm.

Preferably, the female element comprises a straight elongated protruding portion along its shaft; and the roller discs comprises an aperture portion extending out of the center aperture, each aperture portion is mounted on said straight elongated protruding portion.

Preferably, each needle disc comprises two aperture portions positioned on one half of the needle disc thus defining a left and right aperture, wherein each two adjacent needle discs are mounted on the female element in a manner such that one of said adjacent needle disc left aperture is mounted on the straight elongated protruding portion and the other adjacent needle disc right aperture is mounted on the straight elongated protruding portion.

Preferably, the relation between the right and left apertures being mounted result in the needle discs being disposed relatively to one another such that needles which are radially projecting from each needle disc of a pair of non-adjacent needle discs could be connected by an imaginary line drawn parallel to the female element and needles which are radially projecting from each needle disc of a pair of adjacent needle discs could not be connected by an imaginary line drawn parallel to the female element; wherein said pair of non-adjacent needle discs have a single needle disc placed therebetween.

Preferably, the number of needle discs in the roller device is even such that the discs can be assigned with the numbers 1, 2, ... 2n-1, 2n, wherein the needles radially projecting from the even needle discs could be connected by k imaginary lines drawn parallel to the female element 130, wherein k is the number of needles in each needle disc, and wherein the needles radially projecting from the odd needle discs (1, . . . , 2n-1) could be connected by k imaginary lines drawn parallel to the female element and wherein each of said imaginary lines of the even discs does not coincide with any of the imaginary lines of the odd discs.

Preferably, the rotatable structure comprises 4 needle discs and 4 roller discs wherein 3 of said roller discs are placed in between two adjacent needle discs;

Preferably, the number of needle discs in the roller device is odd such that the discs can be assigned with the numbers 1, 2, ... 2n, 2n+1, wherein the needles radially projecting from the even needle discs could be connected by k imaginary lines drawn parallel to the female element 130, wherein k is the number of needles in each needle disc, and wherein the needles radially projecting from the odd needle discs (1, . . . , 2n+1) could be connected by k imaginary lines drawn parallel to the female element and wherein each of said imaginary lines of the even discs does not coincide with any of the imaginary lines of the odd discs.

The present invention relates to a system comprising: a first device as disclosed hereinabove;

and a vibrating micro pigmentation treatment device, comprising a base unit connected to an operation handle, said operating handle comprises a motor and an eccentric system unit fit on said motor adapted to convert the rotational movement of said motor to a distal linear movement of a push pin connected thereto, said push pin is located at the distal portion of said handle;

wherein said push pin is connected to the pin of said first device.

Preferably, the first device pin comprises a dome shaped portion on its proximal end and the push pin comprises a fitting socket on its distal portion.

The present invention relates to a method for providing pigment in the skin giving an appearance of hair follicles on the skin, providing a plurality of needles radially projected from the surface of a roller, the method comprises:
a. Dipping said roller needles in pigment;
b. vibrating said roller causing said needles to vibrate;
c. rolling said vibrating roller on the skin.

Preferably, the skin is the head scalp.

BRIEF DESCRIPTION OF THE DRAWINGS

The present invention is illustrated by way of example in the accompanying drawings, in which similar references consistently indicate similar elements and in which:

FIG. 2 illustrates a device which the present invention connects to.

FIGS. 6a-6c illustrate an embodiment of the roller needle disc element of the present invention.

FIGS. 8a-8c illustrate an embodiment of the spring element of the present invention.

FIGS. 9a-9c illustrate an embodiment of the roller head pin element of the present invention.

FIGS. 10a-10c illustrate an embodiment of the roller head cap element of the present invention.

FIGS. 11a-11c illustrate an embodiment of the roller paint tray element of the present invention.

FIGS. 12a-12d illustrate an embodiment of the roller cover element of the present invention.

FIGS. 20a-20c illustrate an embodiment of the roller head pin element of the present invention.

DETAILED DESCRIPTION OF THE INVENTION

The present invention relates to a device for inserting pigment within the deeper layer of the skin, i.e. the dermis, giving an appearance of hair follicles on the skin.

Figure 1A:
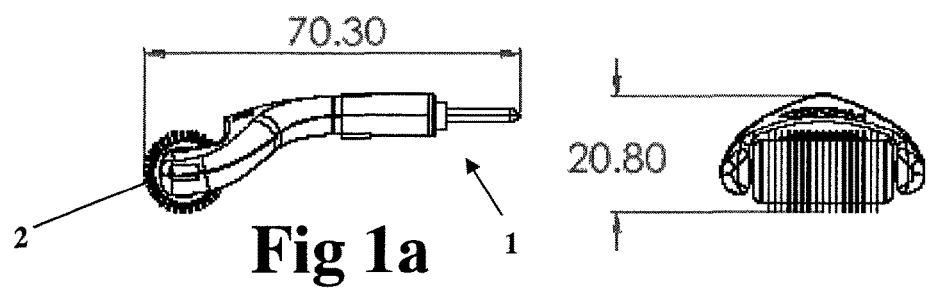
FIGS. 1a-1d illustrate an embodiment of the main structure of the present invention.
Figure 1B:
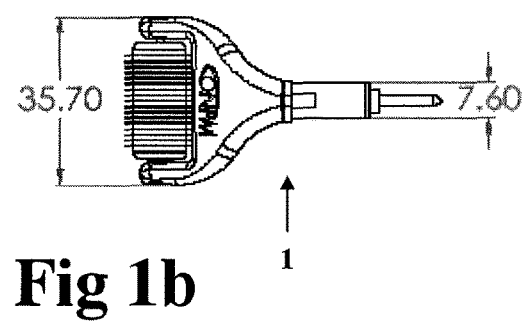

The present invention relates to a device with a smaller but similar structure to that of a roller brush used for painting. The present invention is referred to herein as a roller device 1, Shown in FIGS. 1a, 1b and 1c. The rotating structure 2 that "rolls" and rotates around its central axis comprises a plurality of needles that are intended to be uniformly "rolled" on the skin after being dipped in pigment. The roller device 1 is vibrated causing the penetration of the needles into the skin thus inserting pigment into the second layer of the skin (the dermis). Doing so, it gives an appearance of hair follicles on the skin.

Figure 1C:
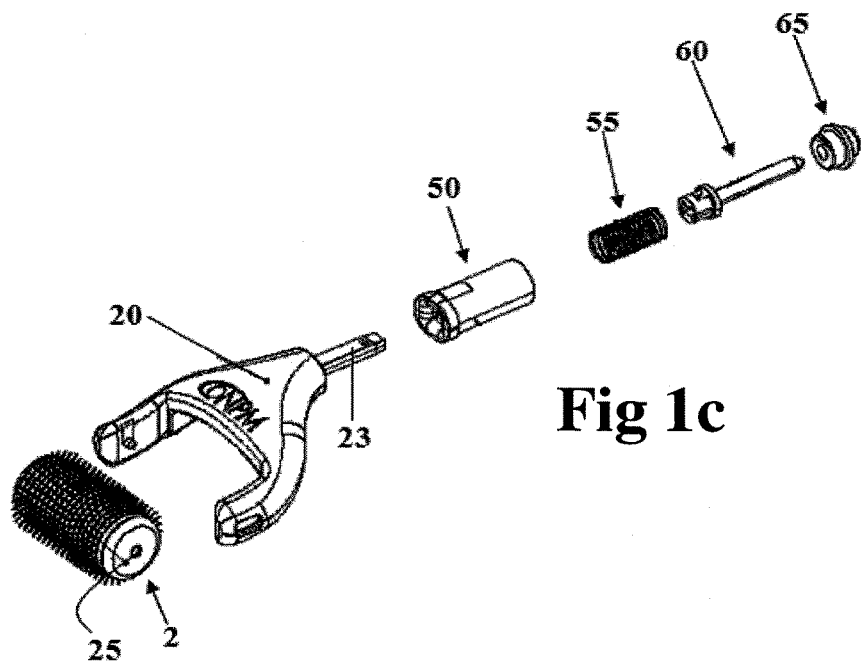

According to an embodiment of the present invention, the roller device 1 (Shown in FIG. 1c) comprises the following elements:
1. Roller head unit 20;
2. Rotating structure 2 comprising:
   a. Roller disc 40;
   b. Roller needle disc 45;
   c. Roller male element 35;
   d. Roller female element 30;
3. Roller tube 50;
4. Spring 55;
5. Roller head pin 60;
6. Roller head cap 65;

Two other elements are also used with the device:
7. Roller cover 70;
8. Roller paint tray 75;

Herein, the distal direction in relation to the roller device 1 and in relation to each of its components (when placed in a correct orientation as shown in FIG. 1*c*) is the direction pointed by the arrow 5 in FIG. 1*c* away from the user. The proximal direction is the opposite direction to which the arrow is pointing to, in relation to the roller device 1 and in relation to its components.

The roller head unit 20 is used as a base for the rotating structure 2 as shown in FIGS. 1*a*, 1*b*, 1*c*, 1*d*, 3*a* and 3*b*. The rotating structure 2 connects to the roller head unit 20 between the distal arms 21*a* and 21*b*. The roller head unit 20 further comprises a proximal portion 23 that connects to the roller tube 50, as will be explained hereinafter.

Figure 3A:
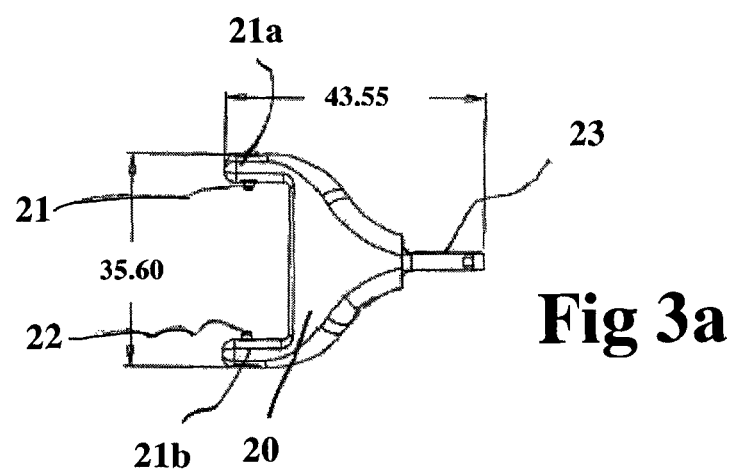
FIGS. 3a-3b illustrate an embodiment of the roller head unit element of the present invention.
Figure 3B:
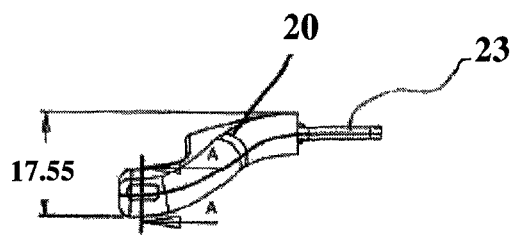
Figure 4A:
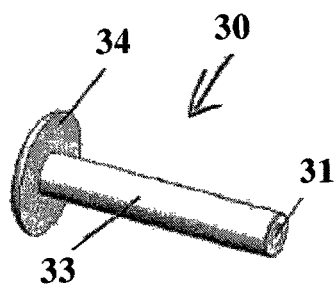
FIGS. 4a-4h illustrate an embodiment of the roller female and roller male elements of the present invention.
Figure 4D:
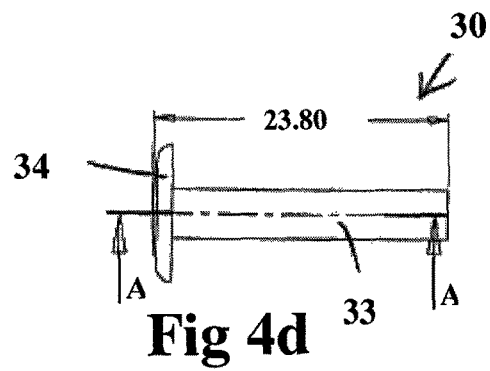
Figure 4B:
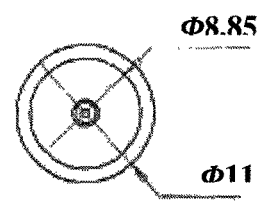
Figure 4C:
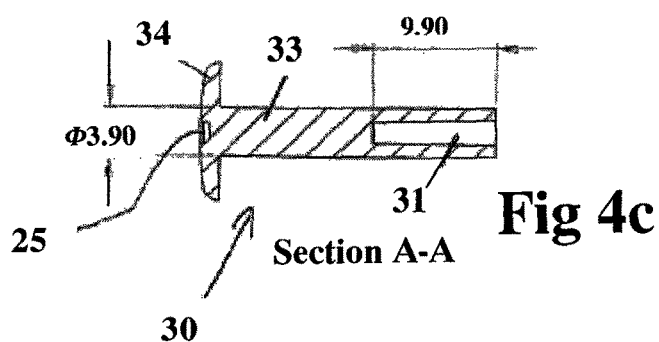
Figure 4F:
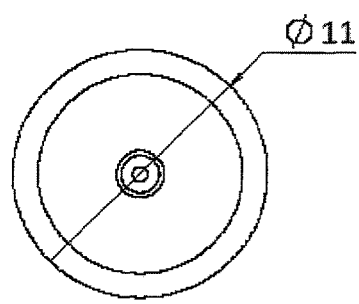
Figure 4E:
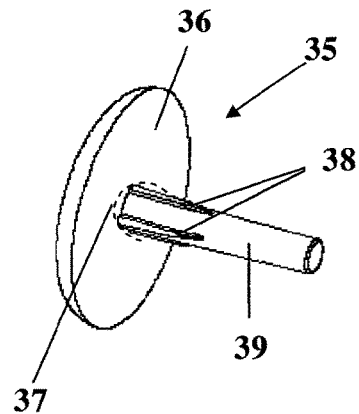
Figure 4G:
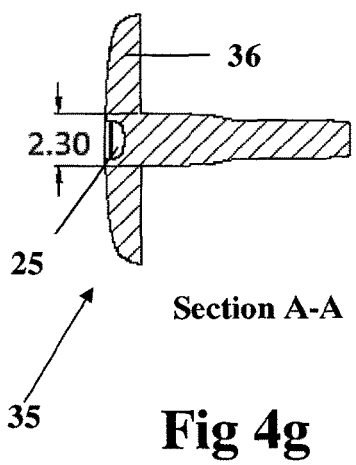
Figure 4H:
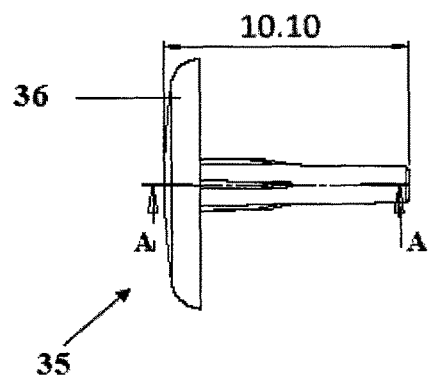
Figure 5A:
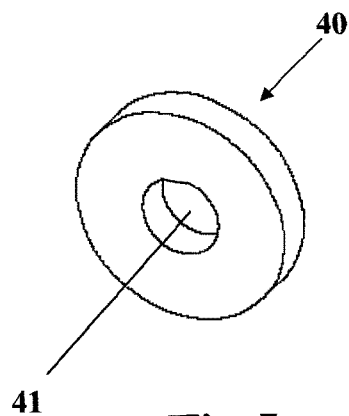
FIGS. 5a-5d illustrate an embodiment of the roller disc element of the present invention.
Figure 5B:
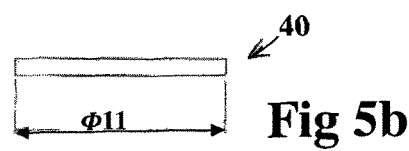
Figure 5C:
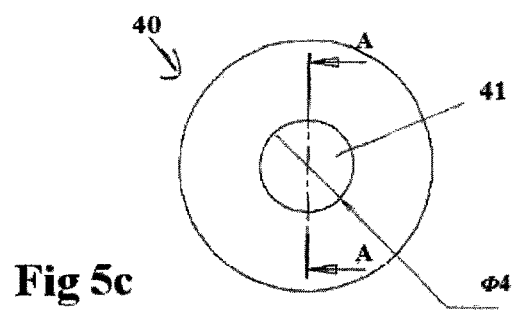
Figure 5D:
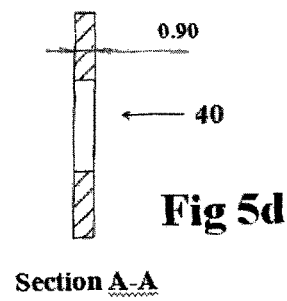
Figure 7B:
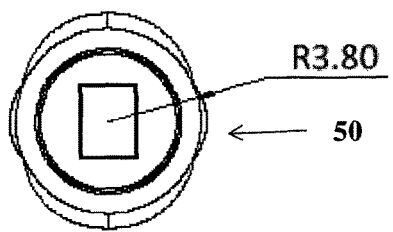
FIGS. 7a-7d illustrate an embodiment of the roller tube element of the present invention.
Figure 7A:
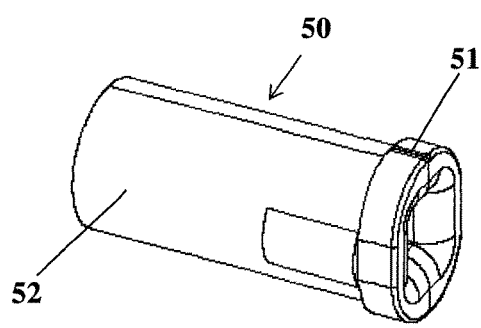
Figure 7C:
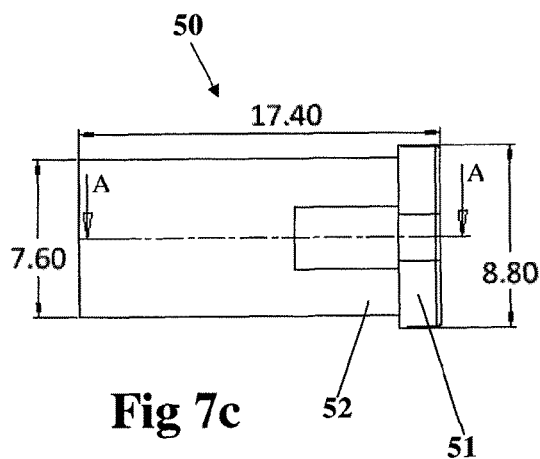
Figure 7D:
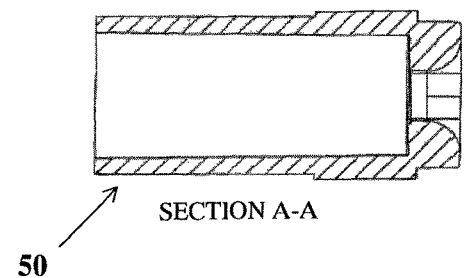

According to one aspect of the present invention, the length of the roller head unit 20 is usually 30-50 mm and preferably 43.55 mm, and its width (the distance between the edges of distal arms 21*a* and 21*b*) is usually 30-40 mm and preferably 35.6 mm. The height of the roller head unit 20 is usually 12-24 mm and preferably 17.55 mm (FIG. 3*b*). Each one of the arms 21*a* and 21*b* comprise a pin 22 fit to hold the female pin 30 and male pin 35 after being placed into depressions 25 comprised in their base portions. The depressions 25 can be shown in FIGS. 1*c*, 4*c*, 4*g* 13*a* and 13*b*. The pins 22 are fit to hold rotating structure 2 by being placed into the depressions 25 thus securing rotating structure 2 to the roller head unit 20.

The roller female element 30 (as shown in FIGS. 4*a*, 4*b*, 4*c* and 4*d*), is usually 18-28 mm and preferably 23.8 mm long. The diameter of the shaft 33 is usually 3-5 mm and preferably 3.9 mm. The length of the hollow portion 31 (within the shaft 33) is usually 7-13 mm and preferably 9.9 mm. The diameter of the roller female element base portion is usually 8-14 mm and preferably 11 mm. The base portion 34 comprises a depression 25 such that pin 22 is fit to be placed in the depression 25 and thus holds and assists securing rotating structure 2 to the roller head structure 20, as explained hereinabove.

Figure 13A:
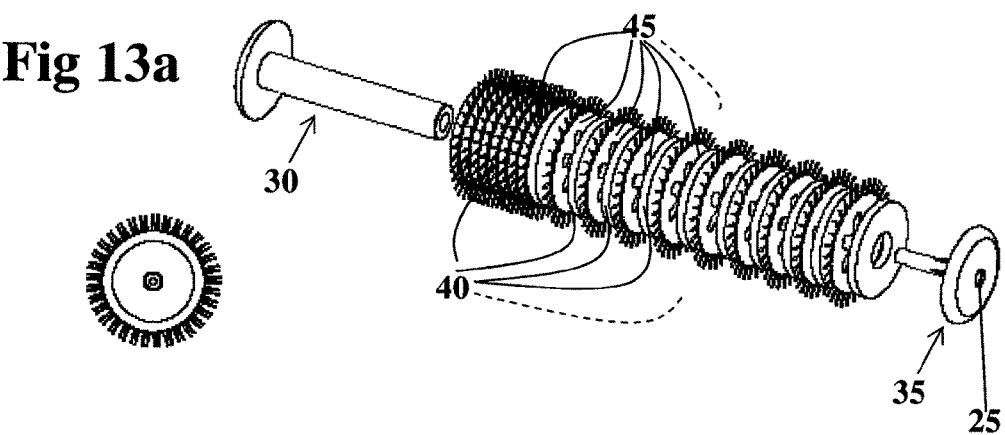
FIGS. 13a-13b illustrate the elements which comprise the rotating structure according to an embodiment of the present invention.
Figure 13B:
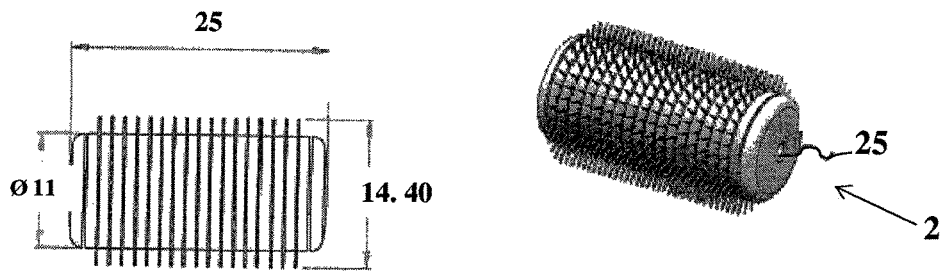

One or more roller needle discs 45 and/or roller discs 40 are threaded through and mounted on the shaft 33 of roller female element 30 as shown in FIGS. 13*a* and 13*b*. When the roller male element 35 is connected and secured to the roller female element 30, pressure is applied on the roller discs 40 and roller needle discs 45 securing them to one another. The roller discs are substantially used as spacers. The distance between needle discs can be enlarged when placing more roller discs 40 between two adjacent roller needle discs 45. The outcome of the distances between the appearances of hair follicle "dots" is accordingly. In a preferred embodiment, one roller disc 40 is placed adjacent to a roller needle disc 45, as shown in FIGS. 13*a* and 13*b*. Then a roller disc 40 is placed, then a roller needle disc 45, etc., until the whole length of the shaft 33 is filled with a plurality of roller needle discs 45 with one roller disc 40 placed in-between two adjacent roller needle discs 45.

FIGS. 5*a*, 5*b*, 5*c* and 5*d* show different angles of the roller disc 40. The diameter of the roller disc 40 is usually 8-14 mm and preferably 11 mm. The diameter of the center aperture 41 is usually 3-5 mm and preferably 4 mm. The thickness of the roller disc 40 is usually 0.1-1.2 mm and preferably 0.9 mm.

FIGS. 6*a*, 6*b* and 6*c* show different angles of the roller needle disc 45. A plurality of needles radially project from the outside circumference of the needle disc. The diameter of the roller needle disc 45 (not including the needles 46) is usually 8-14 mm and preferably 11.2 mm. the lengths of the needles 46 is usually 1.4-1.7 mm and preferably 1.6 mm, what usually prevents the needles of penetrating into more than 1.5 mm of the dermis. The distance between the peeks of two adjacent needles is usually 1-2 mm and preferably 1.37 mm. The thickness of the roller needle disc 45 is usually 0.1-0.3 mm and preferably 0.2 mm.

The roller male element 35 (as shown in FIGS. 4*e*, 4*f*, 4*g* and 4*h*), is usually 5-15 mm and preferably 10.1 mm long. The diameter of the mail base portion 36 is usually 8-14 mm and preferably 11 mm. The diameter of the imaginary circle 37, that encircles the elements 38 attached to the shaft 39 of the roller male, is usually 1.5-3.5 mm and preferably 2.3 mm. The elements 38 assist in securing the roller male 35 to the roller female 30 in a tight efficient manner when the male element 35 is placed within the female element 30. The discs 40 and needle discs 45 are pressed together tightly and secured together when the male element 35 is placed within the female element 30.

The base portion 36 comprises a depression 25 such that pin 22 is fit to be placed in the depression 25 and thus holds and assist securing rotating structure 2 to the roller head structure 20, as explained hereinabove.

In another embodiment, the male 35 and female 30 comprise pins instead of the depressions. Accordingly arms 21*a* and 21*b* comprise depressions instead of the pins 22, such that the pins of the male 35 and female 30 are placed in arms 21*a* and 21*b* depressions.

According to another embodiment of the present invention, the rotating structure is comprised of a cylindrical element, the length of which is adapted to fit between the arms 21*a* and 21*b*. The cylindrical element diameter is preferably similar to that of the roller discs 40 as explained hereinabove. A plurality of small needles, usually 1-3 mm and preferably of the size of 1.5 mm, are attached to the surface of the cylindrical element. The needles are attached by one of the following methods: Sticking, brazing, screwing, adhesion, etc.

The attachment of the rotating structure to the roller head can be by pins and depressions as explained hereinabove (in relation to the rotating structure comprising either pins or depressions) or by placing a bar through the rotating structure wherein the bar is then connected between arms 21*a* and 21*b*. Optionally the bar is placed through a plurality of discs and/or needle discs.

The roller tube 50 (shown in FIGS. 7*a*, 7*b*, 7*c* and 7*d*) is a tubular element that comprises an interior, the shape of which is in accordance with shape of the roller head proximal portion 23, and fit to secure portion 23 therein and prevent circular motion of portion 23. Accordingly it prevents circular motion of the entire roller head unit 20. In a preferred embodiment, the tube interior is rectangular shaped. The width of the rectangular is usually 3-5 mm and preferably 3.80 mm.

The distal portion 51 of the roller tube 50 is preferably thicker than the proximal body 52. The diameter/height of the distal portion is usually 6-12 mm and preferably 8.8 mm wherein the diameter/height of the proximal body 52 is usually 5-10 mm and preferably 7.6 mm. The length of the roller tube 50 is usually 12-22 mm and preferably 17.4 mm.

The roller spring 55 (FIGS. 8*a*, 8*b* and 8*c*) length is usually 8-15 mm and preferably 11.5 mm. The diameter of the spring 55 is usually 4-7 mm and preferably 5.4 mm.

Any suitable elastic element can be used and not necessarily spring 55. According to an embodiment of the present invention, the elastic element is a rubber membrane used instead of spring 55. The rubber membrane comprises elastic properties which gives a similar spring effect to that of spring 55. The dimensions of the rubber membrane are adapted in order to be placed in tube 50 and are preferably similar to the sizes of spring 55.

Figure 9B:
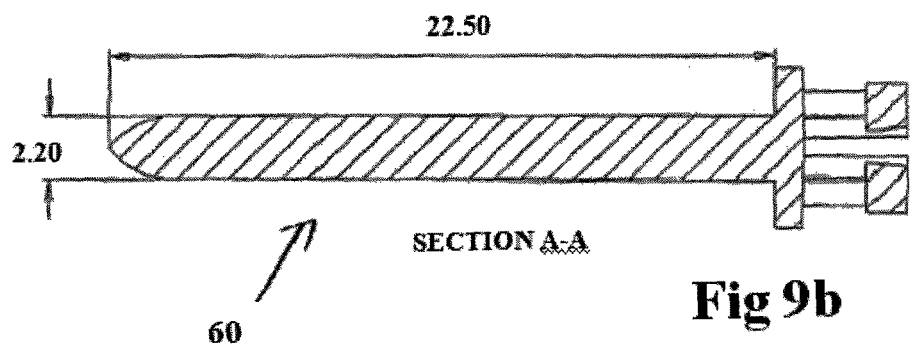
Figure 9C:
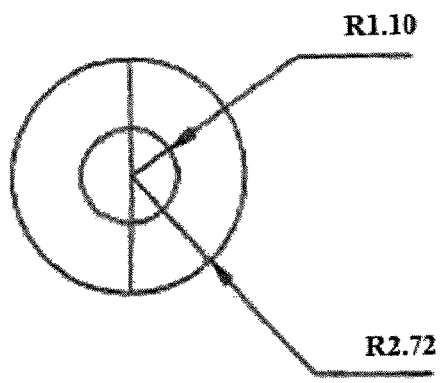

The roller head pin 60 (FIGS. 9a, 9b and 9c) is usually 22-30 mm and preferably 27 mm long. The roller head pin 60 comprises a distal portion 61. The roller head pin 60 further comprises a wide middle portion 62 and a proximal body portion 63, wherein said proximal body portion 63 is usually 20-25 mm and preferably 22.5 mm long. The proximal body portion 63 comprises a dome shaped portion 64. The diameter of the proximal body portion 63 is usually 1.5-4 mm and preferably 2.2 mm, and the diameter of the wide middle portion 62 is usually 3-8 mm and preferably 5.45 mm. The thickness of the wide middle portion 62 is usually 0.5-2 mm and preferably 1 mm.

Figure 10A:
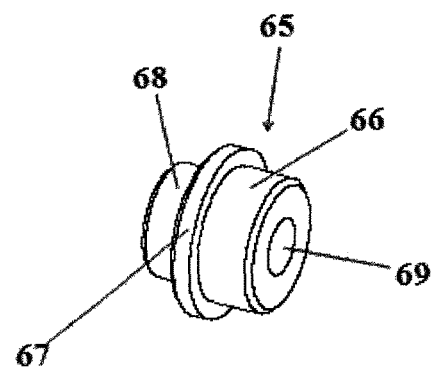

The roller head cap 65 (FIGS. 10a, 10b and 10c) comprises three main disc shaped portions with a common central lumen 69. The roller head cap 65 comprises a distal disc shaped portion 66, usually with a diameter of 4-8 mm and preferably with a 5.95 mm diameter and usually with a thickness of 2-4 mm and preferably a thickness of 2.5 mm. The roller head cap 65 comprises a central disc shaped portion 67 usually with a diameter of 5-10 mm and preferably with a 7.5 mm diameter and usually with a thickness of 0.5-2 mm and preferably a thickness of 1 mm. The roller head cap 65 comprises a proximal disc shaped portion 68 usually with a diameter of 3-8 mm and preferably with a 5 mm diameter and usually with a thickness of 1-3 mm and preferably a 2 mm thickness. The diameter of the common central lumen 69 is usually 2-4 mm and preferably 2.6 mm.

Figure 1D:
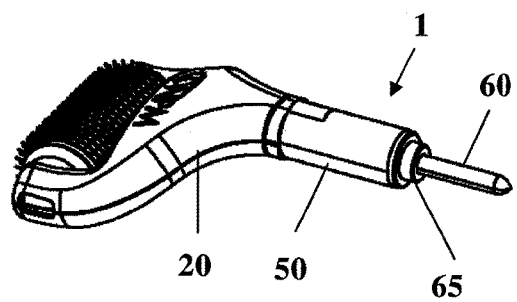

Putting together the roller device 1 can be seen in FIGS. 1c and 1d. The roller head proximal portion 23 is introduced into the roller tube 50 from its distal end and placed and secured therein. The spring 55 is also introduced in the tubular member 50 from its proximal end followed by the roller head pin 60. The roller head pin 60 is placed within the central lumen 69 of cap 65. This is achieved by pushing the cap 65 distally such that the common central lumen 69 it passes along the proximal body portion 63 of the roller head pin 60 until it closes and seals the proximal end of roller tube 50, such that inner lumen of the roller tube 50 encases within its inner lumen, the roller head proximal portion 23, the spring 55, the roller head pin distal portion 61, the wide middle portion 62, the distal portion of the proximal body portion 63 and the distal disc shaped portion 66 of cap 65. The proximal portion of the proximal body portion 63 extends out of the roller cap 65 seal in a proximal direction. This is shown in FIG. 1d.

The spring 55 is placed in-between the wide middle portion 62 on its proximal end and an edge wall portion, within the inner lumen of the roller tube, in its distal end. When the pin 60 is pushed distally it causes the contraction of the spring. Accordingly, the spring applies an outward proximal directed force pushing the roller head pin 60 back proximally.

According to another aspect of the invention (a preferred aspect), the roller device comprises features and sizes that enable a very efficient appliance of pigment to the skin in a manner which provides a very good appearance of hair or hair follicles on the skin. The roller device comprises less needle discs and less needles on each disc and a unique applied needle structure. The task and essence of the elements according to this preferred aspect of the invention are similar to the task and essence of the elements described hereinabove regarding the previous aspect of the invention, however their unique configuration enables a very efficient function of the device. The following description and figures describe this preferred aspect of the invention.

Figure 14A:
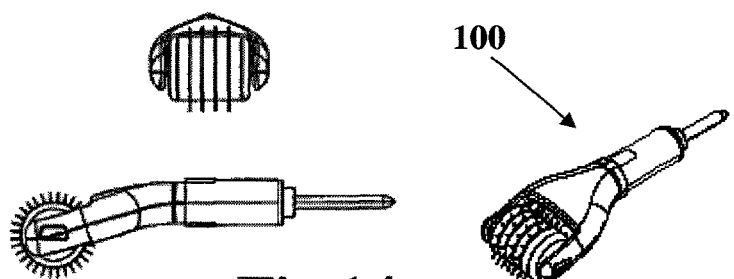
FIGS. 14a-14c illustrate an embodiment of the present invention.
Figure 14B:
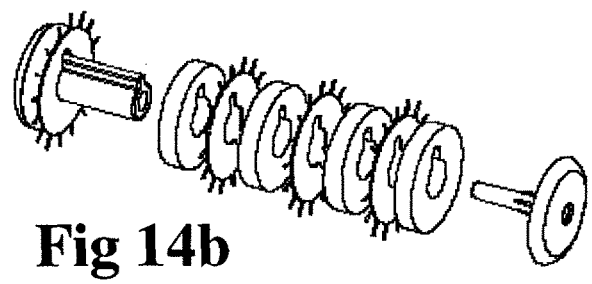
Figure 14C:
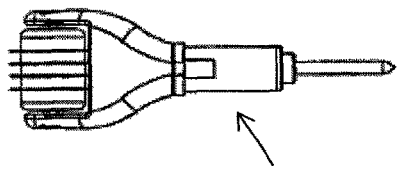
Figure 15A:
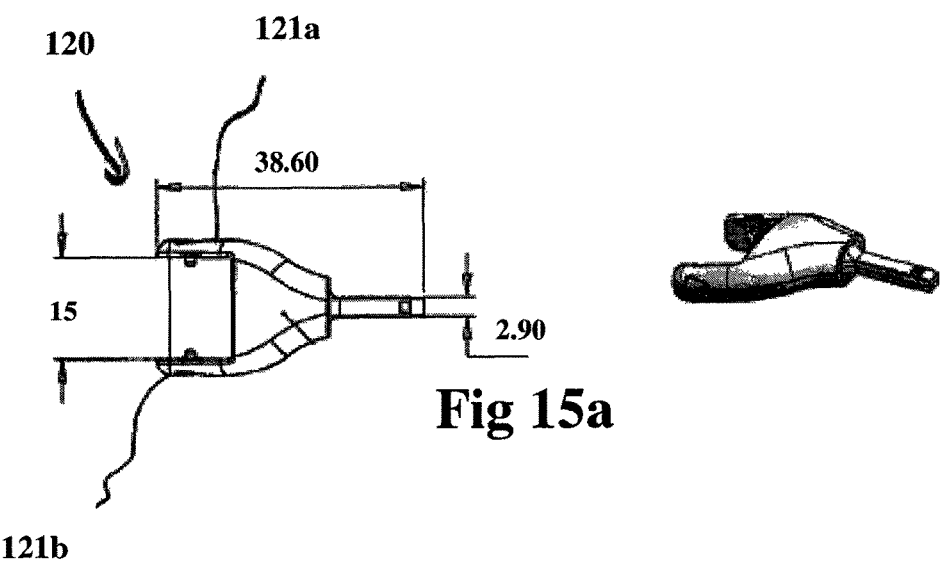
FIGS. 15a-15b illustrate an embodiment of the roller head unit element of the present invention.
Figure 15B:
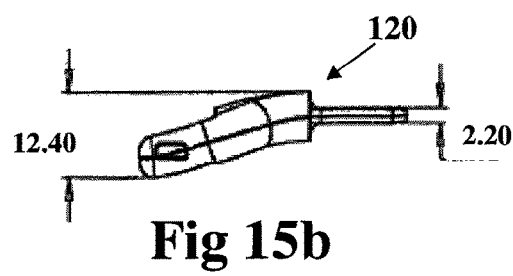
Figure 16A:
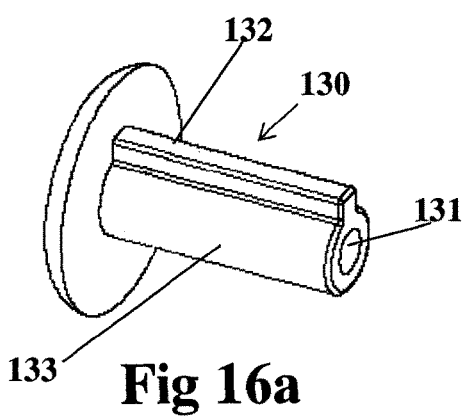
FIGS. 16a-16d illustrate an embodiment of the roller female of the present invention.
Figure 16B:
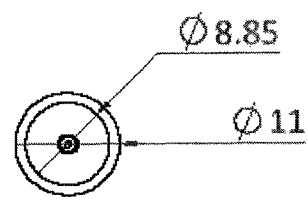
Figure 16C:
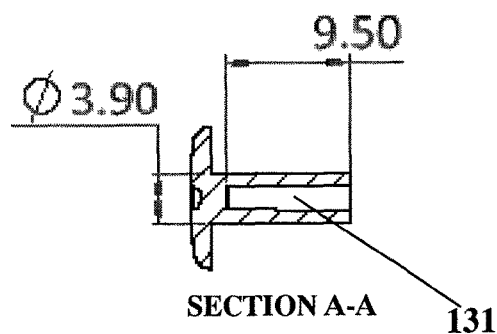
Figure 16D:
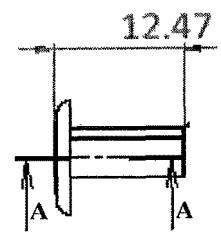

FIGS. 14a, 14b and 14c illustrate an embodiment of a roller device 100 with 4 identical needle discs and 4 roller discs on the rotating structure 102. The length of the roller head unit 120 is usually 30-40 mm and preferably 38.6 mm, and its width (the distance between the edges of distal arms 121a and 121b) is usually 12-18 mm and preferably 15 mm (FIG. 15a). The height of the roller head unit 120 is usually 10-15 mm and preferably 12.4 mm (FIG. 15b).

The roller female element 130 (as shown in FIGS. 16a, 16b, 16c and 16d), is usually 10-15 mm and preferably 12.47 mm long. The length of the hollow portion 131 (within the shaft 133) is usually 7-13 mm and preferably 9.5 mm. The diameter of the roller female element base portion 134 is usually 8-14 mm and preferably 11 mm. The roller female element 130 comprises a straight elongated protruding portion 132 along the shaft 133, that assists in fixating the roller discs and needle discs to the female element 130, such that they will not move out of place.

Figure 17A:
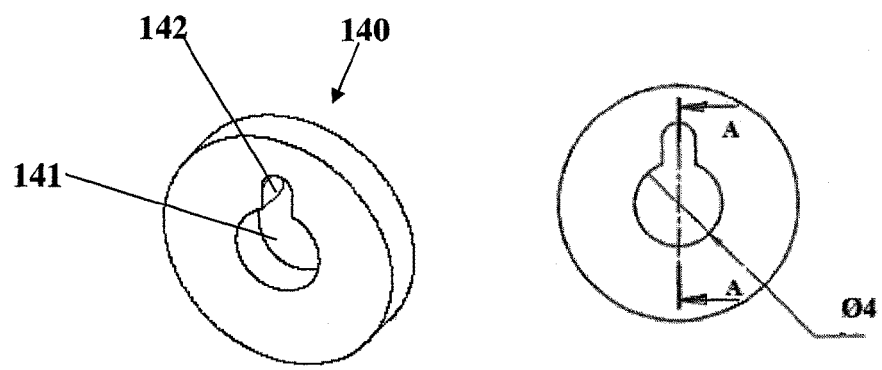
FIGS. 17a-17b illustrate an embodiment of the roller disc element of the present invention.
Figure 17B:
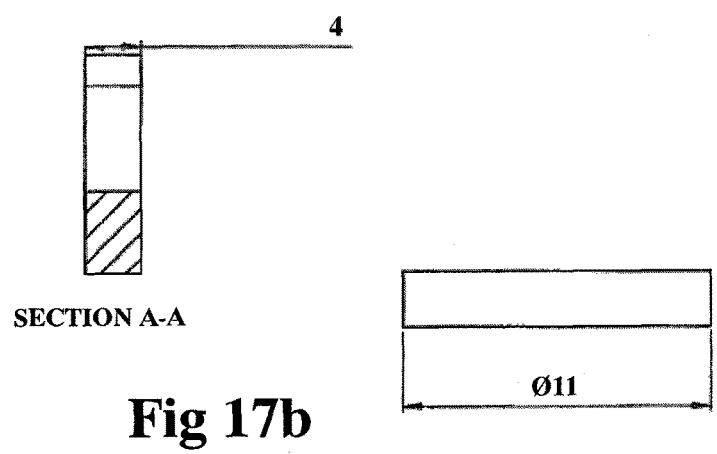

FIGS. 17a-17b illustrate the roller disc 140 which comprises an aperture portion 142 extending out of the center aperture 141, adapted to fit on the straight elongated protruding portion 132. This provides the roller disc 140 with stability such that it will not move out of place. The thickness of the roller disc is usually 1.5-3 mm and preferably 2 mm.

Figure 18A:
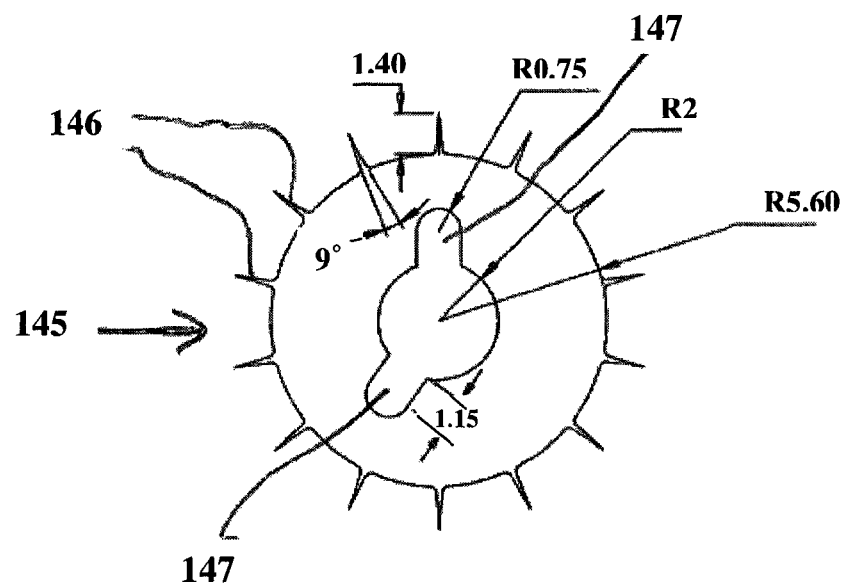
FIGS. 18a-18b illustrate an embodiment of the roller needle disc element of the present invention.

FIG. 18a shows the identical roller needle discs 145. The diameter of the roller needle disc 145 (not including the needles 146) is usually 8-14 mm and preferably 11.2 mm. the lengths of the needles 46 is usually 1.2-1.7 mm and preferably 1.4 mm. Preferably, the distance between each two adjacent needles is the same. The distance between the peeks of two adjacent needles is usually 1-4 mm and preferably 3.12 mm. The thickness of the roller needle disc 145 is usually 0.1-0.4 mm and preferably 0.25 mm. The bottom portion of each needle attached to the needle disc edge is usually 0.15-0.4 mm and preferably 0.23 mm (wherein the needle itself from the peek has about a 9° angle). The number of needles on each disk is usually 12-16 and preferably 14. This number of needles on each disc with the disc diameter size enables a more efficient and natural appearance of hairs and hair follicles when applied on the scalp.

Figure 19A:
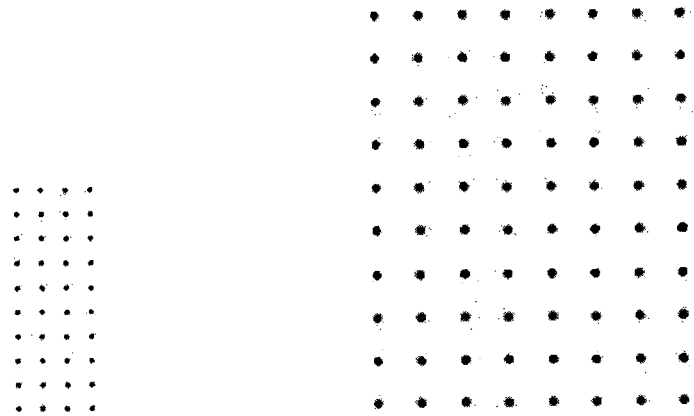
FIGS. 19a-19b illustrate an example of the pigment structure according to an embodiment of the present invention.
Figure 19B:
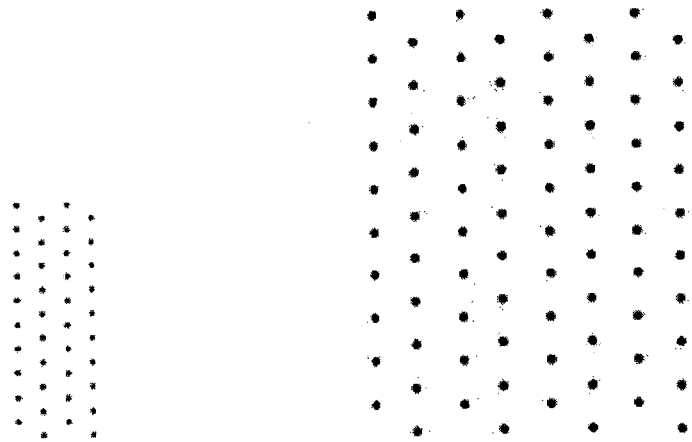
Figure 19C:
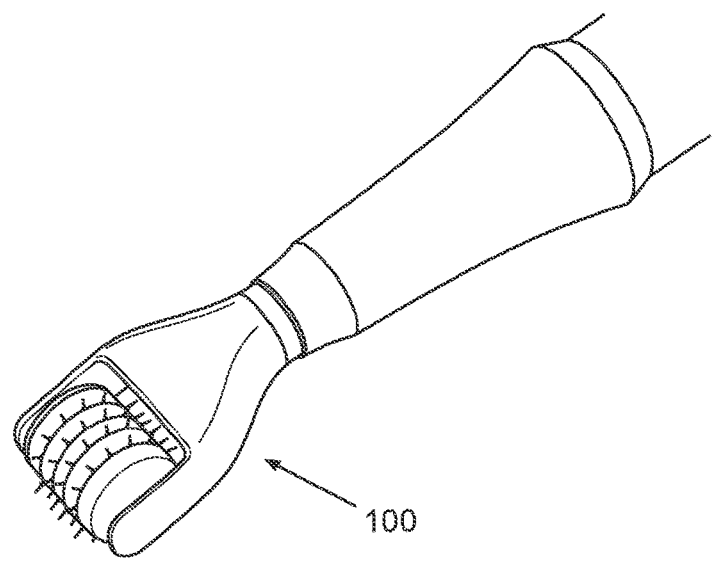
FIGS. 19c-19e illustrate an example of a preferred embodiment of the present invention.
Figure 19D:
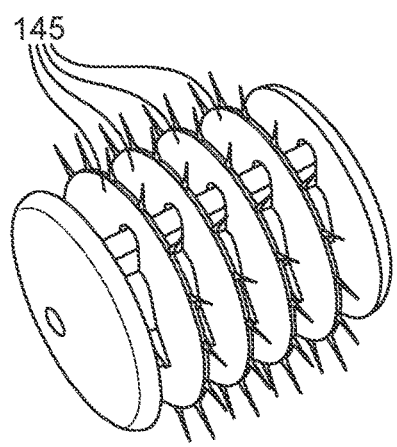
Figure 19E:
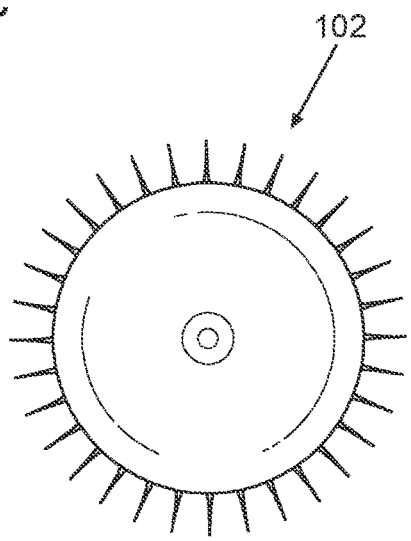

The needle disc 145 comprises one or more aperture portions extending out of the center aperture and preferably two aperture portions 147, as shown in FIG. 18a, each aperture portion is adapted to fit on the straight elongated protruding portion 132. This provides the roller needle disc 145 with stability such that it will not move out of place. The two aperture portions 147 form a two ear like structure (also used herein interchangeably with aperture portion) both tending to be on one half of the needle disc 145 thus defining a left and right aperture (ear). The roller device 100 is constructed by mounting the needle discs 145 on the female pin 130 such that:

a) the first needle disc right ear is mounted on the elongated protruding portion 132,
b) then the first roller disc 140 is mounted,
c) then the second needle disc left ear is mounted on the elongated protruding portion 132,
d) then the second roller disc 140 is mounted,
e) then the third needle disc right ear is mounted on the elongated protruding portion 132, and so on and so forth such that every two adjacent needle discs 145 (having a roller disk 140 therebetween) are each mounted on the elongated protruding portion 132 alternately at opposite ears (one at a right ear one at a left ear). The relation between said right and left apertures being mounted result in that the needles angular rotational positioning is such as follows: The plurality of needle discs that are positioned along the female element 130 are disposed relatively to one another such that needles which are radially projecting from each disc of a pair of non-adjacent discs could be connected by an imaginary line drawn parallel to the female element 130 and needles which are radially projecting from each disc of a pair of adjacent discs could not be connected by an imaginary line drawn parallel to the female element 130 as shown in FIGS. 19c-19e. The pair of non-adjacent needle discs mentioned hereinabove refers to pairs with only one needle disc in-between them, i.e. wherein said non-adjacent discs have a single needle disc placed therebetween.

According to an embodiment of the present invention, the number of needle discs in the roller device is even such that the discs can be assigned with the numbers 1, 2, . . . 2n−1, 2n. Needles radially projecting from the even needle discs (2, . . . , 2n) could be connected by k imaginary lines drawn parallel to the female element 130, wherein k is the number of needles in each needle disc. Needles radially projecting from the odd needle discs (1, . . . , 2n−1) could be connected by k imaginary line drawn parallel to the female element 130, wherein k is the number of needles in each needle disc. The set of imaginary lines of the even discs and the set of imaginary lines of the odd discs do not coincide. Each imaginary line of the even discs does not coincide with any of the imaginary line of the odd discs.

According to an embodiment of the present invention, the number of needle discs in the roller device is odd such that the discs can be assigned with the numbers 1, 2, . . . 2n, 2n+1. Needles radially projecting from the even needle discs (2, . . . , 2n) could be connected by k imaginary lines drawn parallel to the female element 130, wherein k is the number of needles in each needle disc. Needles radially projecting from the odd needle discs (1, . . . , 2n−1) could be connected by k imaginary line drawn parallel to the female element 130, wherein k is the number of needles in each needle disc. The set of imaginary lines of the even discs and the set of imaginary lines of the odd discs do not coincide. Each imaginary line of the even discs does not coincide with any of the imaginary line of the odd discs.

In this manner the roller device is very effective in giving a natural look of hairs or hair follicles on the skin. The alternately left-right ear positioning is constructed such that in a side view, each needle of a needle disc is substantially placed angularly in-between two needles of its adjacent needle disc (preferably, exactly in the middle). This can give a natural look appearance of hairs or hair follicles on the skin. An example of such an efficient appearance structure can be seen in FIG. 19b. If all the needles would be parallel to their adjacent needle disc needles they would form straight vertical and horizontal dotted line arrays giving a more fake appearance (FIG. 19a). FIGS. 19c and 19d show the device with four needle discs in the alternately left-right ear positioning manner. It is clearly seen that each needle on a needle disc is positioned angularly in the middle of two needles of the adjacent needle disc. FIG. 19e shows the aforementioned side view of the rotating structure 102 wherein 16 needles of one needle disc and 16 needles of an adjacent needle disc give a side view of 32 needles.

Figure 18B:
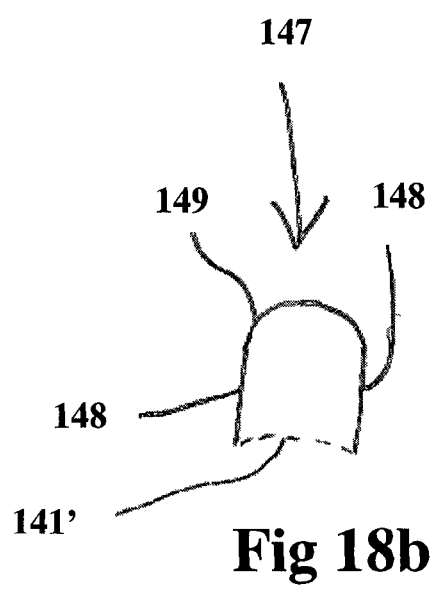

Preferably, the cross-section of aperture portions 142, 147 and straight elongated protruding portion 132 are comprised of two parallel edges 148 an edge portion 149 which is a half circle of radius 0.5-1 mm and preferably 0.75 mm and an imaginary line 141'—the imaginary continuation of the central aperture 141 edge, shown in FIG. 18b.

The roller head pin 160 (FIGS. 20a, 20b and 20c) is usually 22-30 mm and preferably 27 mm long. The roller head pin 160 comprises a distal portion 161. The roller head pin 160 further comprises a wide middle portion 162 and a proximal body portion 163, wherein said proximal body portion 163 is usually 15-25 mm and preferably 18.5 mm long. The proximal body portion 163 comprises a dome shaped portion 164. The diameter of the proximal body portion 163 is usually 1.5-4 mm and preferably 2.4 mm, and the diameter of the wide middle portion 162 is usually 3-8 mm and preferably 5.45 mm. The thickness of the wide middle portion 162 is usually 0.5-2 mm and preferably 1 mm.

According to this preferred aspect of the invention, the male pin, the roller tube, the head cap and the spring comprise the same sizes as described hereinabove in relation to the previous aspect of the invention. Also, other portions of the elements that were not explained herein in regards to the preferred aspect of the invention, usually have the same size as the corresponding portions explained in regards to the first aspect of the invention.

Figure 2:
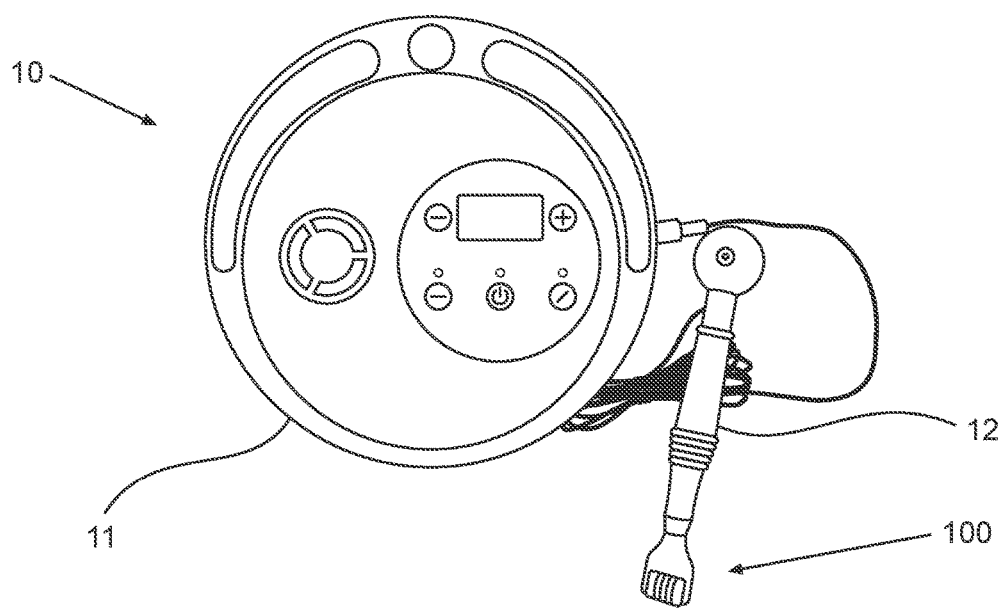

The roller device 1 (and 100) is adapted to connect to a vibrating pigmentation treatment device 10 such as the vibrating micro pigmentation treatment device—ORON 56 model of NPM Ltd., as shown in FIG. 2. The ORON 56 (also adapted to work with a single needle) comprises a base unit 11, an operation handle 12, a foot pedal and a power unit—electric plug. The base unit 11 comprises a control unit and appropriate circuitry for controlling the vibration effect on the operation handle connected thereto. Three connectors are connected to the base unit. A first connector connects the base unit 11 to the power unit electric plug adapted to connect to a wall socket. The second connector connects the base unit 11 to the operation handle 12 and a third connector connects the base unit 11 to the foot pedal.

The base unit 11 comprises a POWER on/off button and a PIECE button that enables function and operation of the operation handle 12 by pressing the foot pedal. The base unit 11 further comprises a LIGHT button that turns on (and off) two LEDs located on the upper portion of the operation handle. The base unit 11 further comprises a "+" button that increases the RPM of the motor comprised in the operation handle 12 thus causing a faster vibration of the operation handle 12 and a "−" button that decreases the RPM of the motor comprised in the operation handle 12 thus causing a slower vibration of the operation handle.

As said, the operating handle 12 comprises a motor and also an eccentric system unit fit on the motor that converts the rotational movement of the motor to a distal linear movement of a push pin connected thereto. The push pin is within the cylindrical (pen) shaped operation handle.

The roller device 1 is adapted to connect to a vibrating pigmentation treatment device 10 such as the ORON 56 model of NPM Ltd., as shown in FIG. 2. The roller device is connected to the, vibrating pigmentation treatment device 10 by its push pin being connected to the roller head pin 60 of the roller device.

The dome shaped portion 64 of the roller head pin 60 is pushed into a fitting socket on the distal part of the push pin (of the eccentric system unit). The push pin connected to the eccentric system unit applies a linear distal pushing force pushing the head pin 60 distally moving the whole device distally. The spring 55 within the roller tube pushes the head pin 60 back proximally. Thus, a vibrating motion is formed wherein periodically, the head pin 60 is pushed distally by the eccentric system unit push pin and pushed back in a proximal direction by the spring 55.

Thus, the whole roller head unit 20 is fluctuated causing a vibration on the rotating structure 2. This vibrating motion enables the needles 46, which have been dipped in the pigment, to penetrate the skin thus inserting pigment into the second layer of the skin (the dermis). Doing so, it gives an appearance of hairs or hair follicles on the skin. The vibration effect assists in pushing the needles into the hard skin.

As said, the "+" and "−" buttons of the vibrating pigmentation treatment device 10 increase/decrease the RPM of the motor. When increased the frequency of the fluctuations of the push pin (connected to head pin 60) is increased accordingly giving a faster vibration effect. When decreased the frequency of the fluctuations of the head pin 60 is decreased accordingly giving a slower vibration effect.

An additional element used in connection with the roller device 1 (and 100) is the roller paint tray 75 (shown in FIGS. 11a, 11b and 11c). The rotating structure 2 is dipped in pigment within the tray before being applied on the skin. The length of the roller paint tray 75 is usually 50-70 mm and preferably 61.5 mm. The width of the roller paint tray 75 is usually 35-55 mm and preferably 44.45 mm. The height of the roller paint tray 75 is usually 10-20 mm and preferably 14.9 mm.

An additional element used in connection with the roller device 1 is the roller cover 70 (shown in FIGS. 12a, 12b, 12c and 12d). The roller cover 70 is used for covering and protecting the rotating structure 2, especially the needles during mobility and when it is packed and cased. The length of the roller cover 70 is usually 30-45 mm and preferably 38.65 mm. The height of the roller cover 70 is usually 16-26 mm and preferably 22.55 mm. The radius of the roller cover 70 circular portion 71 is usually 5-15 mm and preferably 9.5 mm.

According to a preferred embodiment the materials comprising the following elements are as follows:

The roller head 20, the pins 30, 35, 60, tube 50 and cap 65 are preferably comprised of plastic or polycarbonate. The roller discs 40 and needle discs 45 are preferably comprised of stainless steel. The spring 55 is preferably comprised of steal—SAE1090 zinc plated. The elements can also be comprised of other appropriate similar materials as known in the art.

The present invention further relates to a kit comprising the roller device 1 (or 100) as described hereinabove and the tray 75 as described hereinabove and the roller cover 70 as described hereinabove.

The present invention further relates to a method for providing pigment in the skin giving an appearance of hair follicles on the skin. Providing a plurality of needles radially projected from the surface of a roller, the method comprises:

1. Dipping the roller needles in pigment;
2. Vibrating the roller causing said needles to vibrate;
3. Rolling the vibrating roller on the skin.

While some of the embodiments of the invention have been described by way of illustration, it will be apparent that the invention can be carried into practice with many modifications, variations and adaptations, and with the use of numerous equivalents or alternative solutions that are within the scope of a person skilled in the art, without departing from the spirit of the invention, or the scope of the claims.

The invention claimed is:

1. A device for inserting pigment into the skin comprising:
    a. a roller head unit comprising 2 or more distal arms;
    b. a rotatable structure comprising needles extending therefrom, attached to said roller head unit between said distal arms;
    c. a tubular member attached to the proximal end of said roller head unit;
    d. an elastic element placed within the distal portion of the inner lumen of said tubular member; and
    e. a pin placed within said tubular member proximal to said elastic element;
    wherein said pin and said elastic element are vibratingly movable along said tubular member.

2. The device according to claim 1, wherein the rotatable structure comprises:
    a. one or more needle discs, each needle disc comprising a plurality of needles radially projected from the outer circumference of said needle discs, wherein said needle discs are mounted on the shaft of a female element; and
    b. a male element placed in said female element.

3. The roller device according to claim 2, further comprising one or more spacer roller discs mounted on the shaft of the female element.

4. The roller device according to claim 3, further comprising depressions on the base of the male and female elements, and wherein the roller head unit distal arms comprise pins placed in said depressions.

5. The roller device according to claim 3, wherein each needle disc comprises 12-16 needles, and wherein the distance between the roller head unit distal arms is 12-18 mm.

6. The roller device according to claim 5, wherein the female element comprises a straight elongated protruding portion along its shaft; and the roller discs comprises an aperture portion extending out of the center aperture, each aperture portion is mounted on said straight elongated protruding portion.

7. The roller device according to claim 6, wherein each needle disc comprises two aperture portions positioned on one half of the needle disc thus defining a left and right aperture,
    wherein each two adjacent needle discs are mounted on the female element in a manner such that one of said adjacent needle disc left aperture is mounted on the straight elongated protruding portion and the other adjacent needle disc right aperture is mounted on the straight elongated protruding portion.

8. The roller device according to claim 7, wherein the relation between the right and left apertures being mounted result in the needle discs being disposed relatively to one another such that needles which are radially projecting from each needle disc of a pair of non-adjacent needle discs could be connected by an imaginary line drawn parallel to the female element and needles which are radially projecting from each needle disc of a pair of adjacent needle discs could not be connected by an imaginary line drawn parallel to the female element;
    wherein said pair of non-adjacent needle discs have a single needle disc placed therebetween.

9. The roller device according to claim 8, wherein
    the rotatable structure comprises 4 needle discs and 4 roller discs wherein 3 of said roller discs are placed in between two adjacent needle discs.

10. The roller device according to claim 7, wherein the number of needle discs in the roller device is even such that the discs can be assigned with the numbers 1, 2, . . . 2n−1, 2n, wherein the needles radially projecting from the even needle discs could be connected by k imaginary lines drawn parallel to the female element 130, wherein k is the number of needles in each needle disc, and wherein the needles radially projecting from the odd needle discs (1, . . ., 2n−1) could be connected by k imaginary lines drawn parallel to the female element and wherein each of said imaginary lines of the even discs does not coincide with any of the imaginary lines of the odd discs.

11. The roller device according to claim 7, wherein the number of needle discs in the roller device is odd such that the discs can be assigned with the numbers 1, 2, . . . 2n, 2n+1, wherein the needles radially projecting from the even needle discs could be connected by k imaginary lines drawn parallel to the female element 130, wherein k is the number of needles in each needle disc, and wherein the needles radially projecting from the odd needle discs (1, . . ., 2n+1) could be connected by k imaginary lines drawn parallel to the female element and wherein each of said imaginary lines of the even discs does not coincide with any of the imaginary lines of the odd discs.

12. The roller device according to claim 1, wherein the elastic element is a spring.

13. The roller device according to claim 1, wherein the pin extends out of the tubular member distally.

14. The roller device according to claim 1, wherein the pin is configured to be pushed distally, and wherein said pin is configured to be pushed back proximally by the elastic element.

15. The roller device according to claim 1, wherein the pin comprises a wide middle portion placed at the proximal end of the elastic element such that when said pin is pushed distally it causes the contraction of said elastic element.

16. The roller device according to claim 1, wherein the elastic element is a spring, wherein the length of said spring is between 8 and 15 mm and the length of the pin is between 22 and 30 mm.

17. A system comprising:

A first device according to claim 1;

and a vibrating micro pigmentation treatment device, comprising a base unit connected to an operation handle, said operating handle comprises a motor and an eccentric system unit fit on said motor adapted to convert the rotational movement of said motor to a distal linear movement of a push pin connected thereto, said push pin is located at the distal portion of said handle;

wherein said push pin is connected to the pin of said first device.

18. A system according to claim 17 wherein the first device pin comprises a dome shaped portion on its proximal end and the push pin comprises a fitting socket on its distal portion.

19. A method for providing pigment in the skin giving an appearance of hair follicles on the skin, providing a plurality of needles radially projected from the surface of a roller, the method comprises:

a. Dipping said roller needles in pigment;

b. vibrating said roller causing said needles to vibrate; and c. rolling said vibrating roller on the skin.

20. A method according to claim 19, wherein the skin is the head scalp.

* * * * *